(12) United States Patent
Penny et al.

(10) Patent No.: US 11,598,739 B2
(45) Date of Patent: Mar. 7, 2023

(54) METHODS AND SYSTEMS FOR HIGH FIDELITY ELECTRICAL TOMOGRAPHIC PROCESSES

(71) Applicants: Ryan Wade Penny, Cambridge, MA (US); Gregory Arthur Passa, New York, NY (US)

(72) Inventors: Ryan Wade Penny, Cambridge, MA (US); Gregory Arthur Passa, New York, NY (US)

(73) Assignee: PENNY PRECISION LLC, Cambridge, MA (US)

( * ) Notice: Subject to any disclaimer, the term of this patent is extended or adjusted under 35 U.S.C. 154(b) by 853 days.

(21) Appl. No.: 16/351,253

(22) Filed: Mar. 12, 2019

(65) Prior Publication Data

US 2019/0285562 A1    Sep. 19, 2019

Related U.S. Application Data

(60) Provisional application No. 62/642,572, filed on Mar. 13, 2018.

(51) Int. Cl.
*G01N 27/02* (2006.01)
*G01N 27/04* (2006.01)

(52) U.S. Cl.
CPC ......... *G01N 27/026* (2013.01); *G01N 27/045* (2013.01)

(58) Field of Classification Search
CPC .... G01N 27/026; G01N 27/045; G01N 27/08; G01N 33/20; G01N 27/04; A61B 5/0536; A61B 5/0809; A61B 5/6823; A61B 5/053
See application file for complete search history.

(56) References Cited

U.S. PATENT DOCUMENTS 5,984,023 A * 11/1999 Sharma ............... E21B 49/02
175/58
8,508,238 B2    8/2013 Mahalingam et al.
(Continued)

FOREIGN PATENT DOCUMENTS

CN    102364420 B    6/2012
CN    103604843 A    1/2017
(Continued)

OTHER PUBLICATIONS

Trevor York, "Status of Electrical Tomography in Industrial Applications", Proceedings of SPIE vol. 4188 ,2001. (Year: 2001).*
(Continued)

*Primary Examiner* — Alexander Satanovsky
*Assistant Examiner* — Asm Fakhruddin

(57) ABSTRACT

Methods and systems for high fidelity electrical tomographic processes are provided for herein. Specifically, the use of a purpose-selected fluid configuration is described, used to fill the void space between mechanically fixed sensing electrodes and the target object to sense and reconstruct. In some embodiments, this fluid configuration enhances or masks changes in electrical measurements in response to certain materials known or suspected to exist within the sensed volume. In other embodiments, a plurality of fluid configurations may be employed to improve the quality of reconstruction, or resolve additional spatial dimensions. Exemplary applications in medicine and manufacturing are also provided.

16 Claims, 12 Drawing Sheets

(56) References Cited

U.S. PATENT DOCUMENTS

| | | | |
|---|---|---|---|
| 8,594,763 B1 * | 11/2013 | Bibian | A61B 5/283 600/383 |
| 8,614,707 B2 | 12/2013 | Warsito et al. | |
| 9,207,198 B2 | 12/2015 | Wang et al. | |
| 10,378,941 B2 | 8/2019 | McCann et al. | |
| 10,920,919 B2 | 2/2021 | Vreenegoor et al. | |
| 2004/0127796 A1 * | 7/2004 | Chalana | A61B 8/0833 600/449 |
| 2010/0097374 A1 * | 4/2010 | Fan | G06T 11/006 324/658 |
| 2010/0148798 A1 | 6/2010 | Wang et al. | |
| 2014/0231077 A1 * | 8/2014 | Rivero | E21B 47/113 166/250.12 |
| 2016/0091448 A1 | 3/2016 | Soleimani | |

FOREIGN PATENT DOCUMENTS

| | | | | |
|---|---|---|---|---|
| DE | 102004004604 B4 * | 12/2016 | | A61B 5/721 |
| WO | WO 2004/052169 | * | 6/2004 | A61B 5/05 |
| WO | WO-2004052169 A2 * | 6/2004 | | A61B 5/0035 |
| WO | WO2016201427 | * | 12/2016 | C09K 8/62 |
| WO | WO-2016201427 A1 * | 12/2016 | | C09K 8/80 |

OTHER PUBLICATIONS

M. Zhang and M. Soleimani, Imaging floating metals and dielectric objects using electrical capacitance tomography, Measurement (Journal), Jul. 21, 2015, all pages, vol. 74.

Trevor York, Status of Electrical Tomography in Industrial Applications, SPIE Process Imaging for Automatic Control, (Journal), 2001, All Pages, vol. 4188.

Wuqiang Yang, Design of electrical capacitance tomography sensors, Measurement Science and Technology (Journal), 2010, All Pages, vol. 21.

Andronikou, Savvas and McHugh, Kieran and Abdurahman, Nuraan and Khoury and Mngomezulu, Victor and Brant, William E. and Cowan, Ian and Mculloch, Mignon and Ford, Nathan, Paediatric radiology seen from Africa. Part I: providing diagnostic imaging to a young population, Pediatric Radiology, 2011, 41:811-825.

Andronikou, Savvas and Mngomezulu, Victor, Paediatric radiology seen from Africa. Part II: recognizing research advantages in a developing country, Pediatric Radiology, 2011, 41:826-831.

Andryieuski, Andri and Kuzetsova, Svetlana and Zhukovsky, Sergi and Kivshar, Yuri and Lavrienko, Water: Promising Opportunities For Tunable All-dielectric Electromagnetic Metamaterials, Scientific Reports, 2015, vol. 5, Article No. 13535.

Barber, D and Brown, B, Errors in reconstruction of resistivity images using a linear reconstruction technique, Clinical Physics and Physiological Measurement, 1988, 9:101-104.

Bate, David, Aspe Tutorial: Getting the best from X-ray CT and CT Metrology with AM Parts, Presentation, Nikon Metrology, 2016.

Bhatia, Risha and Schmolzer, Georg M and Davis, Peter G and Tingay, David G, Electrical impedance tomography can rapidly detect small pneumothoraces in surfactant-depleted piglets, Intensive Care Medicine, 2012, 38:308-315.

Bodenstein, Marc and David, Matthias and Marstaller, Klaus, Principles of electrical impedance tomography and its clinical application, Critical Care Medicine, 2009, vol. 37, No. 2.

Boverman, G. and Isaacson, D and Saulnier, G and Newell J, Methods for Compensating for Variable Electrode Contact in EIT, IEEE Transactions on Biomedical Engineering, 2009, vol. 56, No. 12.

Brown, B.H., Electrical impedance tomography (EIT): a review, Journal of Medical Engineering & Technology, 2003, vol. 27, No. 3, 97-108.

Chatziioannidis, I and Samaras, T and Nikolaidis, N, Electrical Impedance Tomography: a new study method for neonatal Respiratory Distress Syndrome?, Hippokratia, 2011, 15, 3: 211-215.

Cherepenin, V and Karpov, A and Korjenevsky, A and Kornienko, V and Mazaletskaya, A and Mazourov, D and Meister, D, A 3D electrical impedance tomography (EIT) system for breast cancer detection, Physiological Measurement, 2001, 22:9-18.

Diamond, G. G. and Hutchins, D. A. and Gan, T. H. and Purnell, P. and Leong, K. K., Single-sided capacitive imaging for NDT, Electrostatic Inspection, Insight, 2006, vol. 48, No. 12, 724-730.

Evangelidis, Marianthe and Ma, Lu and Soleimani, Manuchehr, High Definition Electrical Capacitance Tomography for Pipeline Inspection, Progress in Electromagnetics Research, 2013, vol. 141, 1-15.

Geibprasert, Sasikhan and Pongpech, Sirintara and Jiarakongmun, Pakorn and Shroff, Manohar and Armstrong, Derek and Krings, Timo, Radiologic Assessment of Brain Arteriovenous Malformations: What Clinicians Need to Know, RadioGraphics, 2010, 30:483-501.

Hallaji, Milad and Seppanen, Aku and Pour-Ghaz, Mohammad, Electrical impedance tomography-based sensing skin for quantitative imaging of damage in concrete, Smart Materials and Structures, 2014, vol. 23, Article No. 085001.

Heikkinen, Lasse M and Vilhunen, Tanja and West, Robert M and Vauhkonen, Simultaneous reconstruction of electrode contact impedances and internal elecliical properties: II. Laboratory experiments, Measurement Science and Technology, 2002, vol. 13, 1855-1861.

Herman, Rhett, An introduction to electrical resistivity in geophysics, American Journal of Physics, 2001, vol. 69, No. 9, 943-952.

Holder, David S, Electrical Impedance Tomography, Methods, History and Applications, Institute of Physics Publishing, 2005, Philadelphia.

Huang, Sm and Xie, CG and Thorn, R and Snowden, D and Beck, MS, Design of sensor electronics for electrical capacitance tomography, Brunel University Research Archive, 1992, Brunel University, London, UK.

Hyun, Jin-Gul and Lee, Sangyong and Cho, Sung-Dong and Paik, Kyung-Wook, Frequency and Temperature Dependence of Dielectric Constant of Epoxy/BaTiO3 Composite Embedded Capacitor Films (ECFs) for Drganic Substrate, Proceedings Electronic Components and Technology, 2005, IEEE, 1241-1247.

Klein, Lawrence A. and Swift, Calvin T., An improved model for the dielectric constant of sea water at microwave frequencies, IEEE Transactions on Antennas and Propagation, 1977, vol. 25, No. 1, 104-111.

Kolehmainen, V and Vauhkiben, M and Karjalainen, P. A. and Kaipio, J. P., Assessment of errors in static electrical impedance tomography with adjacent and trigonometric current patterns, Physiological Measurement, 1997, vol. 18, 289-303.

Kolehmainen, Ville and Lassas, Matti and Ola, Petri and Siltanen Samuli, Recovering Boundary Shape and Conductivity in Electrical Impedance Tomography, Inverse Problems and Imaging, 2013, vol. 7, No. 1, 217-242.

Li, Y and Holland, D J, Fast and Robust 3D electrical capacitance tomography, Measurement Science and Technology, 2013, vol. 24, Article No. 105406.

Malkin, Robert A., Design of health care technologies for the developing world, Review of Biomedical Engineering, 2007, 9:567-87.

Maryott, Arthur A. and Smith, Edgar R., Table of Dielectric Constants of Pure Liquids, National Bureau of Standards, United States Department of Commerce, 1951.

Mauriello, Paolo and Monna, Dario and Patella Domenico, 3D geoelectric tomography and archaeological applications, Geophysical Prospecting, 1998, 46:543-570.

Munns, I.J. and Georgiou, G.A., Ultrasonic and radiographic NDT of butt fusion welds in polyethylene pipe, Plastic Pipes IX, Heriot-Watt University, 1995, 551-560.

Ngambi, TM and Borgstein, ES, Epidemiology of paediatric trauma admissions at queen Elizabeth central hospital, Blantyre, Malawi Medical Journal, 2005, vol. 17, 5-6.

Passa, Gregory and Penny, Ryan and Podlaha-Murphy, Elizabeth, Improving the Spatial Resolution of Electrical Capacitance Tomography by Utilizing Different Chemical Media of High Dielectric Constant, Poster Presentation, Northeastern University Research Innovation and Scholarship Exposition, 2012.

(56) References Cited

OTHER PUBLICATIONS

Pauwels, Ernst K. J and Foray, Nicolas and Bourguignon, Michel H, Breast Cancer Induced by X-ray Mammography Screening? A Review Based on Recent Understanding of Low-Dose Radiobiology, Medical Principles and Practice, 2016, vol. 25:101-109.

Sawicki, B and Grzywacz, Electrical Impedance Tomography through an ambient fluid as a solution for electrode contact problem, Przegląd Elektrotechniczny, 2012, vol. 88, No. 4, 129-131.

Soleimani, M and Stewart, V. J., and Budd, C. J., Crack detection in dielectric objects using electrical capacitance tomography imaging, Insight-Non Destructive Testing and Condition Monitoring, 2011, vol. 53, No. 1, 21-24.

Styra, D. and Babout, L, Improvement of AC-based Electrical Capacitance Tomography Hardware, Elektronika ir Elektrotechnika, 2010, vol. 7, 47-50.

Teschner, Eckhard and Imhoff, Michael and Leonhardt, Steffen, Electrical Impedance Tomography: The realization of regional ventilation monitoring, 2014, Dragerwerk AG & Co., Lubeck, Germany.

Voss, Antti and Pour-Ghaz, Mohammad and Vauhkonen, Marko and Seppanen, Aku, Electrical capacitance tomography to monitor unsaturated moisture ingress in cement-based materials, Cement and Concrete Research, 2016, vol. 89, pp. 158-167.

Williams, R. A. and Beck, M. S., Process Tomography, Butterworth-Heinemann Ltd, 1995, Oxford, England.

Xiaohui, Hu and Min, Yang and YI, LI and Wuqiang, Yang and Manrique De Lara, Maria, An impedance-analyser-based multichannel imaging system and its applications, IEEE International Workshop on Imaging Systems and Techniques, 2008.

Yang, WQ and Peng, Lihui, Image Reconstruction Algorithms for Electrical Capacitance Tomography, Measurement Science and Technology, 2003, vol. 14, No. 1.

Ye, Z and Banasiak, R and Soleimani, M, Planar array 3D electrical capacitance tomography, Insight, 2013, vol. 55, No. 12, 675-680.

Yin, Ziaokang and Hutchins, David A and Chen, Guoming and Li, Wei, Preliminary studies on the design principles of capacitive imaging probes for non-destructive evaluation, International Journal of Applied Electromagnetics and Mechanics, 2013, vol. 42, 447-470.

* cited by examiner

METHODS AND SYSTEMS FOR HIGH FIDELITY ELECTRICAL TOMOGRAPHIC PROCESSES

CROSS REFERENCE TO RELATED APPLICATION

The present disclosure claims priority to U.S. Provisional Application No. 62/642,572, entitled "Methods and Systems for High Fidelity Electrical Impedance Tomography," which was filed on Mar. 13, 2018, and which is incorporated by reference herein in its entirety.

BRIEF SUMMARY

The present disclosure relates to methods and systems for preforming tomography on an object by differentiating materials by their response to an electric field, and more particularly relates to manipulating the sensing fields to optimally sense certain materials or regions of the object.

BACKGROUND

Electrical Capacitance, Resistance, and Impedance Tomography (ECT, ERT, and EIT, respectively) have long been prized for providing safe, high speed tomographic data for medicine and industry. These techniques rely on differentiating materials by their response to electric fields, ultimately generating an image illustrating the geometry and composition of the subject. In this disclosure, we describe how these measurements are most often taken between a series of plate-like electrodes. Depending on the sensing modality, there exists either a void space between the electrodes and target, or the electrodes are attached directly thereto. The boundary conditions presented by either of these cases make performing accurate image reconstruction difficult; however, the enclosed inventions mitigate these challenges by introducing a fluid specifically chosen for its electrical properties between the electrodes and target. ECT, ERT, and EIT may all be augmented through careful selection of this fluid, including by increased sensitivity, clutter rejection, or enabling non-contact resistance measurements.

These techniques differentiate regions of differing materials based upon their electrical properties, and then use this information to digitally reconstruct the material distribution in 2D or 3D. The two primary properties of interest are a material's resistance to the flow of electrical current (resistivity), and the polarizability of the material, as quantified by its dielectric constant. One skilled in the art will recognize the similarities between reconstruction based upon these properties, thus an electrical measurement of these properties is taken to include measurement of at least one electrical property of the reconstructed volume. Below, we derive a mathematical framework to describe how these electrical measurements may be performed and used to tomographically reconstruct a material distribution.

Derivation of the relevant fields proceeds from Poisson's Equation for electrostatics, as given in Eqn. 1a. Here, $\nabla \cdot D(r)$ is a vector equation representing the divergence of the electric displacement field and $\rho(r)$ is the free charge density. Because bulk matter carries no net charge, one can set $\rho$ equal to 0, and the equation thereby reduces to Laplace's Equation. $D(r)$ is given in two common forms by Eqn. 1b, where $\chi_e$ is the electric susceptibility, $\epsilon_0$ is the permittivity of free space (vacuum), $\epsilon_r(r)$ is the relative permittivity distribution, and $E(r)$ is the electric field vector. Last, one inserts Eqn. 1 for E, where V is the scalar electric potential and A is the magnetic vector potential. As these sensing modalities do not incorporate a time-varying magnetic field, A is set equal to 0. The result is given in Eqn. 1d, which essentially states that the divergence of the product of the permittivity distribution and potential gradient must be zero. It is this equation that supports our following discussion on sensing capacitance and resistance.

$$\nabla \cdot D(r) = \rho(r) = 0 \qquad \text{Eqn. 1a}$$

$$D(r) = \epsilon_0 E(r)(1 + \chi_e) = \epsilon_0 \epsilon_r(r) E(r) \qquad \text{Eqn. 1b}$$

$$E(r) = -\nabla V - \frac{\partial A}{\partial t} \qquad \text{Eqn. 1c}$$

$$\nabla \cdot [\epsilon_0 \epsilon_r(r) \nabla V(r)] = 0 \qquad \text{Eqn. 1d}$$

The forward problem of calculating capacitance between two conductors is formulated using the field equation derived above (Eqn. 1d). This process begins by calculating the net charge $Q_j$ sensed at the $j^{th}$ conductor due to an electric potential applied to the $i^{th}$ conductor, making use of Gauss' Law (Eqn. 2a) in which the charge inside a volume is determined from integrating D over the volume's surface, $\Gamma$. The resulting expression in expanded form is shown in Eqn. 2b. Finally, capacitance is defined to be the ratio of charge to voltage. Thus dividing Eqn. 2b by the voltage applied to the $i^{th}$ conductor yields Eqn. 2c: the capacitance $C_{ij}$ between conductors i and j.

$$Q = \oint_\Gamma D \cdot da \qquad \text{Eqn. 2a}$$

$$Q_j = -\epsilon_0 \oint_{\Gamma_j} \epsilon_r(r) \nabla V(r) \cdot da \qquad \text{Eqn. 2b}$$

$$C_{ij} = -\frac{\epsilon_0}{V_i} \oint_{\Gamma_j} \epsilon_r(r) \nabla V(r) \cdot da \qquad \text{Eqn. 2c}$$

Non-conductive materials, or insulators, are commonly referred to as dielectrics, and, like all bulk matter, they carry zero net electric charge. However, these materials are very much able to interact with electric fields through dipole interactions. Consider the electric field about a water molecule; the molecule is electrically net neutral, but the electrons cluster about the oxygen atom, leaving the hydrogen atoms more exposed. This causes a nonzero electric field around the molecule, known as a dipole moment. In an electric field, no net displacement occurs, as the electron's attraction to regions of positive potential are perfectly offset by the attraction of the positive nucleus to regions of more negative potential. There is, however, a net torque about the molecule, rotating it to oppose the electric field, such that the hydrogen nuclei point towards negative potential and the more negative oxygen atom points oppositely.

Like water, acetone has a fairly strong dipole moment owing to the increased negative potential around the oxygen atom. Conversely, the fairly uniform, symmetric nature of butane gives it little inherent dipole nature, however, molecules, and even single atoms, can have dipoles induced by external fields. This effect occurs as the electron cloud about an atom or molecule is slightly attracted to regions of positive potential, and the positive nucleus is pulled in the opposite direction. Polarization due to this effect is typically weaker as compared to molecules with innate dipole moments; for example, butane has a dielectric constant of approximately 1.4.

This process is called polarization, and the symbol P represents the net dipole moment per unit volume. P is proportional to E for most dielectrics in moderate E fields, as shown in Eqn. 3a. Electrical susceptibility is an experimentally measured quantity that describes how strongly a material exhibits polarization in response to an electric field. In practice, the shorthand in Eqn. 3b is often employed, in which the quantity $\in_r$ is known as the relative permittivity or dielectric constant, as first employed here in Eqn. 1b. This simplifies calculations like those above by adding the electric field that caused the polarization to the field resulting from the polarization.

Beyond these considerations, the dielectric constant of a material is a function of a great number of variables, however, temperature and frequency are among the most influential. FIG. 1 illustrates the effects of these parameters on the permittivity and conductivity of water. Dielectric constant falls at high temperature as this increase in molecule kinetic energy interferes with the polarization process. While the physical nature of these curves at high frequency are beyond the scope of this document, they clearly hold implications for sensing impedance at microwave frequencies.

Metals feature markedly different behavior in an electric field than that of dielectric materials. In general, the more mobile electrons in a metal will shift such that the external electric field is perfectly canceled inside the material. ECT is then able to resolve the exterior surfaces of a metallic object, however, it is practically impossible to see inside them with capacitive techniques.

$$P = \in_0 \chi_e E \quad \text{Eqn. 3a}$$

$$\in_r = 1 + \chi_e \quad \text{Eqn. 3b}$$

The field equation for resistance calculations, given in Eqn. 4a is practically identical to that developed above for the capacitance case, albeit with the dielectric distribution replaced with the conductivity distribution σ(r). The first step in calculating the resistance between two conductors is to integrate the gradient of the electric potential over a path P(r) that begins on the $i^{th}$ electrode and terminates on the $j^{th}$, as shown in Eqn. 4b. Once this change in voltage is known, the resistance between the two conductors is simply calculated by dividing by the current $I_{ij}$ that flows between them, as per Ohm's law (Eqn. 4c).

$$\nabla \cdot [\sigma(r) \nabla V(r)] = 0 \quad \text{Eqn. 4a}$$

$$\Delta V_{ij} = \int_{P(i)}^{P(j)} \nabla V_i(r) \cdot dl \quad \text{Eqn. 4b}$$

$$R_{ij} = \frac{\Delta V_{ij}}{I_{ij}} \quad \text{Eqn. 4c}$$

The resistance, or conversely conductivity, of a material depends on a great deal of factors, and can arise in several ways. Ionic solutions, for example, conduct electricity as ion movement can transport electric charge. This mechanism is distinct from the conduction process in metallic materials, in which marginally bound electrons are free to float from one atom to the next. Even materials that are conventionally thought of as excellent insulators, such as plastics or glass, exhibit finite resistance, permitting differentiation by this property. Again, as shown in FIG. 1, these properties are strong functions of temperature and frequency. This figure illustrates that water, an insulator at low and high frequencies, becomes moderately conductive at microwave frequencies.

Due to the great number of applications of electrical tomography, one skilled in the art will appreciate that there are a great multitude of sensor designs for performing this process. All that is required to perform these techniques are meaningful measurements across the electrodes, and a mathematical representation by which to perform the reconstruction. Indeed, sensors often used in ERT for geological prospecting often consist of little more than a series of conductive spikes driven into the earth with a known geometric spacing. Here, we outline relevant designs as well as more recent works aimed at generating more complex reconstructions. FIG. 2 displays the topology of a typical electrical tomography instrument. At the core of each device is a plurality of conductive electrodes 220, commonly copper, that are arranged about the target object 210. Each of these plates is connected to an electrical readout 250 (sensing electronics), with cables for electrode excitation 230 and measurement 240, and that readout is capable of using electrodes to simultaneously supply a signal to an electrode and record the response at the others. This readout interfaces with a computer 280 for image reconstruction, which sends control signals to the readout 270 and receives data therefrom 260. The number and location of electrodes varies between applications, but the principle of reciprocity limits the N independent electrode-pairs for measurement to in a system of M electrodes as determined by Eqn. 5.

$$N = \frac{M(M-1)}{2} \quad \text{Eqn. 5}$$

Some of the most common applications of ECT, along with the other electrical methods, are imaging two-phase fluid flow in pipelines, cyclones, and reaction vessels. Imaging these processes lend themselves to the system depicted in FIG. 2, in which the electrodes 220 are regularly spaced on a circle about a pipe or vessel. If the container wall is non-conductive, electrodes may be placed around its exterior. However, it may be more optimal to place the electrodes inside the vessel wall, and this must be done if the vessel is made of a conductive material.

Medical implementations of electrical tomography typically employ EIT using directly attached electrodes. For example, electrodes may be adhesively attached to a patient, enabling impedance measurement across the chest to assess lung function. Other approaches use a belt-like system to maintain contact between electrodes and the patient. These approaches are not without their drawbacks, namely that electrode position and contact resistance are uncertain, which greatly degrade recovered image quality. As a final note, this figure illustrates that a sub-region of a target object may be imaged without resolving the entire object.

More sensitive capacitance metering tools have given rise to more complex imaging systems. The conventional systems described above provide a 2D representation of the material distribution within the sensor. The axial resolution is typically extremely poor (on the order of centimeters), making useful 3D reconstruction of an object practically impossible. However, 3D ECT has recently become an area of intense research, in which small sensing electrodes are placed about a volume, enabling three-dimensional determination of permittivity distribution. A typical example is illustrated in FIGS. 3a-3b, that displays a cubic scanner with 9 electrodes 310 per side. Such a device is capable of 1431 unique measurements, providing a fairly detailed reconstruction of objects in the sensing volume 320. Still other approaches are similar to the typical axial layout, albeit with several rings of electrodes along the axial direction of a pipe-like vessel. 3D reconstructions are also commonly applied in ERT and EIT applications, including subterranean imaging and performing mammograms.

Image reconstruction is the process by which the individual impedance measurements between sensing electrodes are interpreted in view of the sensor geometry, and are thus turned into a meaningful description of a target's composition. This process is rather difficult, as the number of measurements is typically much lower than the number of pixels in the reconstructed image. This class of problems are mathematically described as under-determined, ill-defined, or ill-posed, as there is no way to exactly determine the permittivity of a single pixel, and in-fact, an infinite multitude of material distributions are capable of producing identical capacitance readings. As a result, the image is always something of a best-guess, although careful implementation can make it a very good one. Below, Linear Back Projection (LBP) is described in the context of ECT. This class of reconstruction methods are most commonly employed, and provides the clearest context for explanation of the enclosed inventions. One skilled in the art will recognize more advanced algorithms are a topic of ongoing research and development, and will appreciate how the present disclosure may function with them.

LBP begins by determining the sensitivity maps between pairs of electrodes. In the forward problem, these matrices describe how the measured capacitance between two electrodes changes as a function of the dielectric distribution within the sensor on a voxel-by-voxel basis. These matrices have, in general, three dimensions, as the electric field between the electrodes has components in all spatial directions. However, for many ECT systems, especially those used in pipeline imaging, the sensors are long enough as compared to their diameter to safely neglect variation in the axial direction. For ease of illustration this simplified 2D reconstruction is discussed, however, the basic process is identical upon addition of a third spatial dimension.

Although sensitivity maps can be determined experimentally, they are often computed via finite element simulation of the sensor geometry. The electric field is determined both by exciting the $i^{th}$ electrode with voltage V and grounding the $j^{th}$ electrode, yielding the electric field $E_i(x, y)$ as a function of the x-y location within the sensor, and reversing the measurement yields the field $E_j$. The sensitivity $S(x, y)$ is then the integral of the dot product of these fields over the pixel's area, as shown in Eqn. 6. A typical result of this simulation process is shown in FIG. 4, where the sensitivity map 420 best detects changes in dielectric distribution in the highlighted band between the two electrodes 410.

$$S(x, y) = \frac{\int_A E_i \cdot E_j da}{V^2}$$ Eqn. 6

The linearized forward problem of ECT—determining the capacitance between electrodes based upon a defined permittivity distribution—is described by the matrix Eqn. 7a, where C are the intra-electrode capacitances, S are the sensitivity maps rearranged into stacked, 1D row vectors, and P is the permittivity distribution within the sensor. Of course, the objective here is to solve the inverse problem, Eqn. 7b, for P using the measured capacitances C. In effect, one is solving Eqn. 2c in reverse, making use of known C and $\nabla V$ to solve for $\in_r(r)$. As alluded to above, this problem is difficult because there is not enough information in, for example, the 28 measurements from an 8 electrode sensor to solve for the exact permittivity value of each pixel in a 100×100 pixel grid. Mathematically, this means that the inverse matrix of S cannot be calculated to solve the equation shown in Eqn. 7b, because the inverse of a non-square matrix (28×10000 in this example) simply does not exist.

$$C = SP$$ Eqn. 7a $$S^{-1}C = P$$ Eqn. 7b

To overcome this difficulty, LBP uses a construct known as the pseudo-inverse (or Moore-Penrose Pseudo-Inverse) to calculate the best least-squares estimate of $S^{-1}$, often denoted as $S^\dagger$. Many methods for calculating this matrix exist; however, a technique called SVD (Singular Value Decomposition) is often employed. The form of this decomposition is shown in Eqn. 8a. Beginning from the left, $V^T$ contains eigensensitivity maps of the sensor, $\Sigma$ contains the singular values of each of these eigenvectors (relative importance of an eigenvector to S as a whole), and U contains eigenvectors matching each weighted eigensensitivity back to the original sensitivities. The pseudo-inverse is then calculated according to Eqn. 8b, in which E is inverted using a well-defined procedure for square, diagonal matrices. Equation 8c then gives the least-squares estimate of P. P is then the linear, weighted sum of sensitivity matrices that best satisfies the measurements in C. The result of the reconstruction, because it is an estimate and not a perfect representation of P, is denoted as $\hat{P}$.

$$S = U\Sigma V^T$$ Eqn. 8a $$S^\dagger = V\Sigma^{-1}U^T$$ Eqn. 8b $$S^\dagger C = \hat{P}$$ Eqn. 8c Singular value decomposition is an optimal method for calculating $S^\dagger$, as it permits regularization of the solution. In this example, regularization is a means for recovering much of the high spatial frequency information that is otherwise washed out by LBP, without amplifying sensor noise. A process initially conceived for regularization of geophysical ERT data by Tikhonov in 1943 (Tikhonov Regularization), has become a standard method for computing the regularized pseudo-inverse as described in Eqn. 9. Functionally, this process is identical to the procedure stated above; however, the matrix of singular values ($\Sigma$) has been reweighted according to Eqn. 9b, where $\alpha$ is an empirically determined regularization factor. This equation reduces the relative importance of eigensensitivites with large weights—that provide less spatial detail—in comparison to those with smaller weights that contain higher spatial frequency data.

$$S^\dagger = VDU^T$$ Eqn. 9a

-continued $$D_{ii} = \frac{\sum\limits_{ii}}{\frac{\sum\limits_{ii}^2}{2} + \alpha^2}$$  Eqn. 9b A more complex regularization may make use of other assumptions or prior knowledge about the reconstruction. Incorporation of a prior becomes an issue of encoding it as a matrix B, then minimizing the quantity in Eqn. 10 as a function of $\hat{P}$, where λ is an empirically determined constant to adjust the strength of regularization.

$$\|S\hat{P} - C\| + \lambda \|B\hat{P}\|$$  Eqn. 10

More advanced methods of image reconstruction are often seen in high performance ECT reconstruction. For example, a priori knowledge can be used to improve the reconstruction, especially when sensing known materials. These algorithms often operate iteratively, in which one material or another is assigned to a given pixel based upon the initial sensor readings. The forward problem Eqn. 7a is then solved on this estimated distribution, yielding a set of capacitance values for that distribution. The difference between forward projected C and actual C give an error signal, which can be used to refine the material assignments, and then perform another iteration.

BRIEF DESCRIPTION OF THE DRAWINGS

The disclosure will be more fully understood by way of the accompanying drawings, in which.

DETAILED DESCRIPTION

The present invention provides a method for enhancement of electromagnetic tomographic processes through careful selection of a fluid configuration that fills the void space between the sensing electrodes and target. By way of non-limiting examples, this fluid configuration may be selected to enhance the sensitivity of a sensor or mask materials that are not of interest. Moreover, these techniques may be employed in selection of a medium to couple stationary, fixed ERT and EIT sensors to targets, eliminating the difficulties of attaching electrodes to irregularly shaped, fragile, or moving objects. We also note that instead of simply using the increased sensor fidelity to enable the use of low-cost, low-resolution readouts, this technology directly enables smaller, more numerous electrodes to be used, thereby improving the spatial resolution (axial, in-plane, or both) of these technologies. Finally, we note that novel image reconstruction methods are possible in which impedance measurements are taken with a series of different fluids, and the results used to obtain higher-fidelity reconstructions than would otherwise be possible.

As previously mentioned, this invention provides for a fluid configuration filling the void space between the sensing electrodes and target, selected to enhance electrical measurements of the sensed volume. A fluid configuration is comprised of at least one fluid, with this at least one fluid occupying a specified region of the sensed and reconstructed volume. Several fluids may be used simultaneously, such as an immiscible oil floating above a water-filled region. Generally, a fluid may be comprised of a mixture of several components, such as gases, liquids, solids capable of suspension, or a component capable of dissolving in a component also thus incorporated, by way of non-limiting examples. Any inhomogeneous component is optimally sufficiently finely divided and dispersed as to not be resolved by the sensor. Such mixtures offer the ability to finely tune electrical properties. Other benefits or considerations for fluid configuration may include, protection of a reactive target material from oxidation or other contamination. Exemplary, non-limiting embodiments will now be described to provide an understanding of the function and use of fluid configurations in tomographic reconstruction of a volume by electrical properties.

Figure 1:
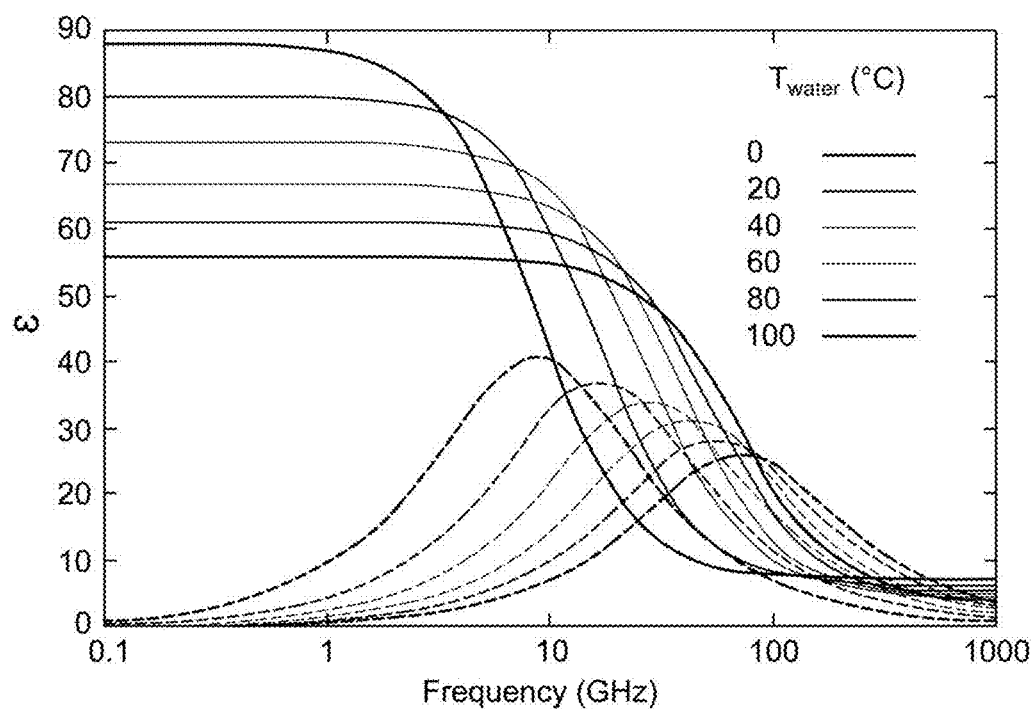
FIG. 1 is a plot representing the dielectric constant and resistivity of water as a function of temperature and measurement frequency.
Figure 2:
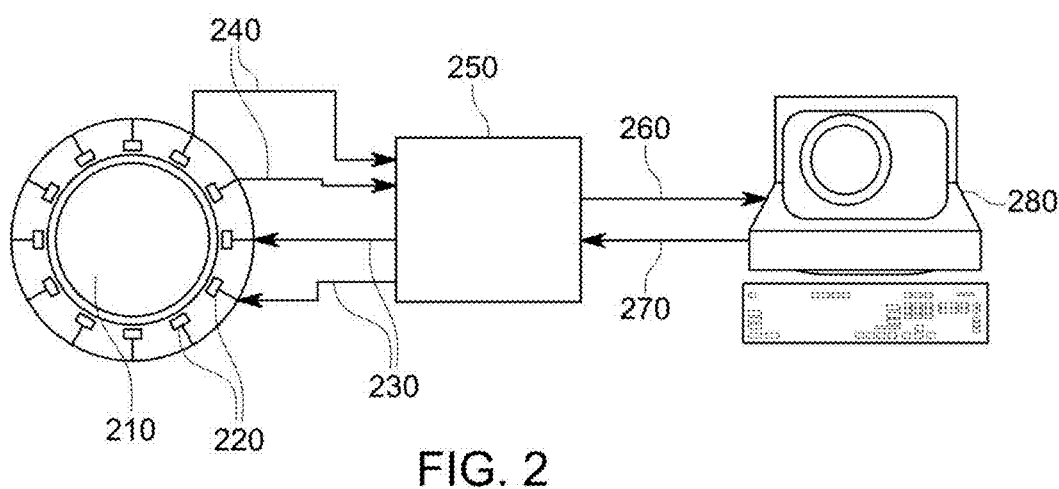
FIG. 2 illustrates the components of a typical ECT system.
Figure 3A:
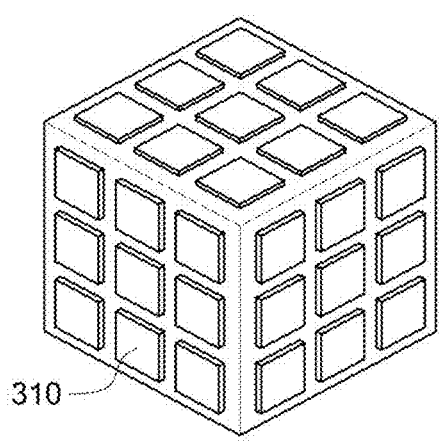
FIGS. 3a-3b illustrate a 3D ECT system.
Figure 3B:
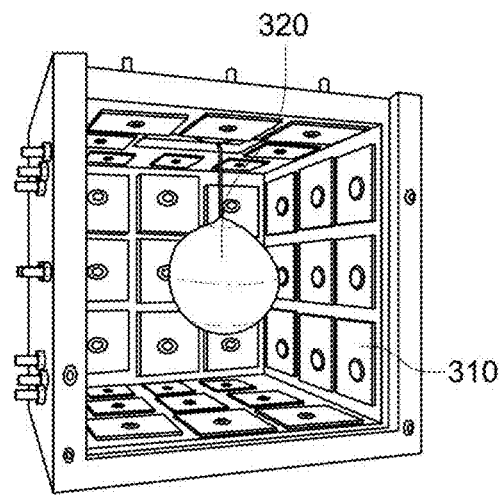
Figure 4:
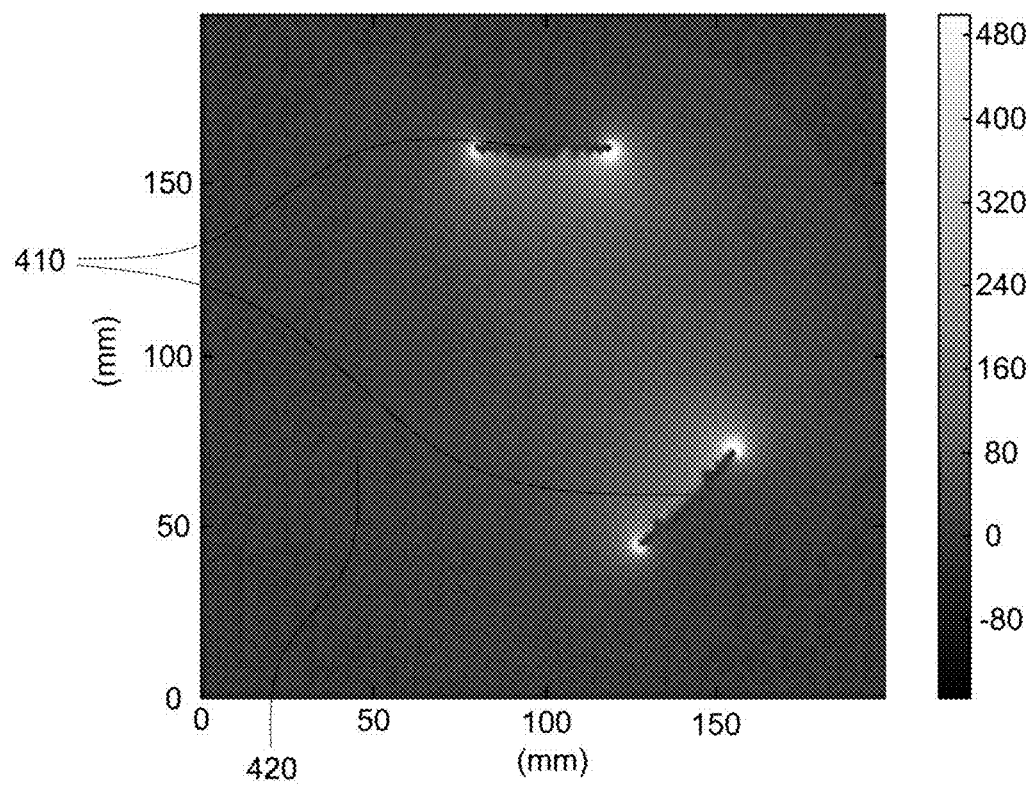
FIG. 4 plots the sensitivity map between two electrodes of an ECT system.
Figure 5:
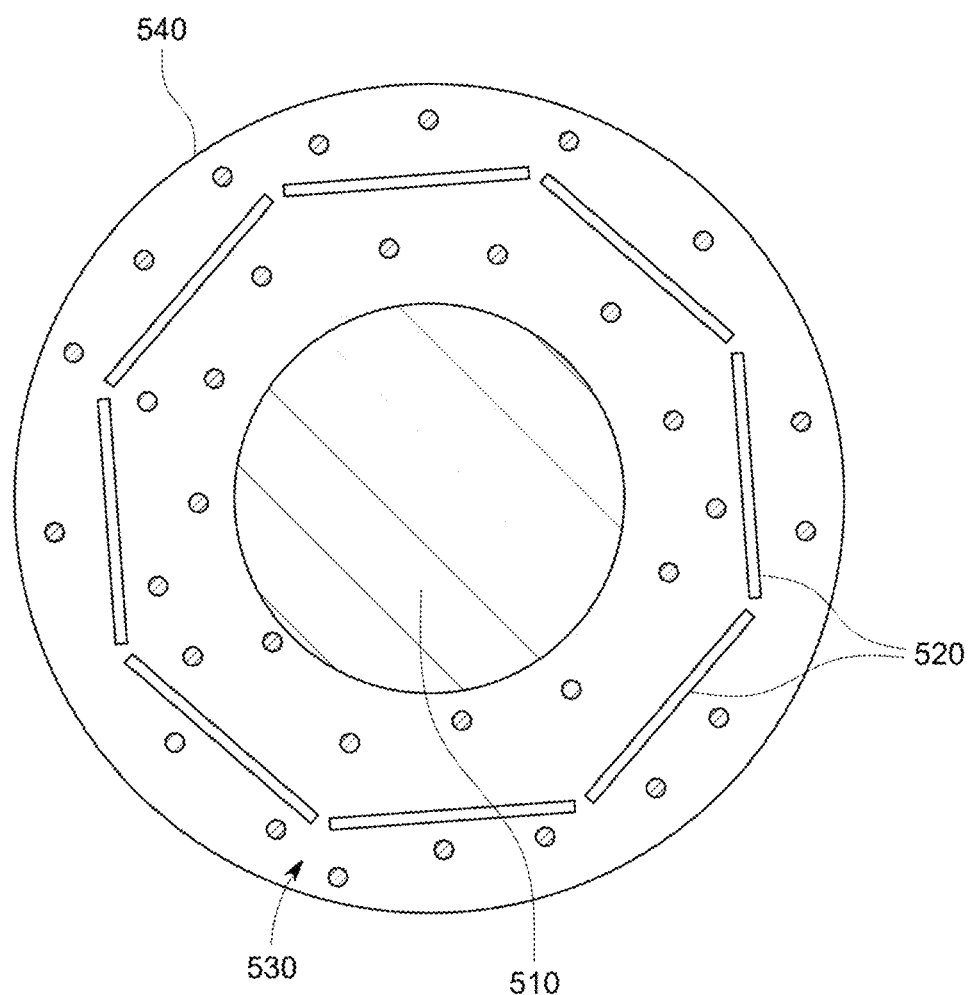
FIG. 5 shows a fluid configuration that may be used to contract a target material.

One aim of choosing a fluid configuration to fill the void-space in an EIT, ERT, or ECT sensor may be to provide contrast against the target. Schematically, this is illustrated in FIG. 5, in which an object of interest 510, placed within the sensing electrodes 520, is shown to displace the fluid 530 within the sensor. This fluid is contained within the sensor by a vessel 540. As an example, water, with a dielectric constant of 80.37, provides excellent contrast to many common polymers, including polyvinyl chloride and polyethylene (3.18 and 2.25, respectively). In the conventional ECT device employed simulated herein, the net change in capacitance within the sensor results from displacing air with polyethylene, for a net change of Δ=1.25 over the volume of the tube. Filling this void space with water results in a change of Δ=79.37 in dielectric constant when the pipe is inserted. Of course, the reverse idea, choosing a low dielectric fluid to contrast a high permittivity target is possible as well.

Figure 6:
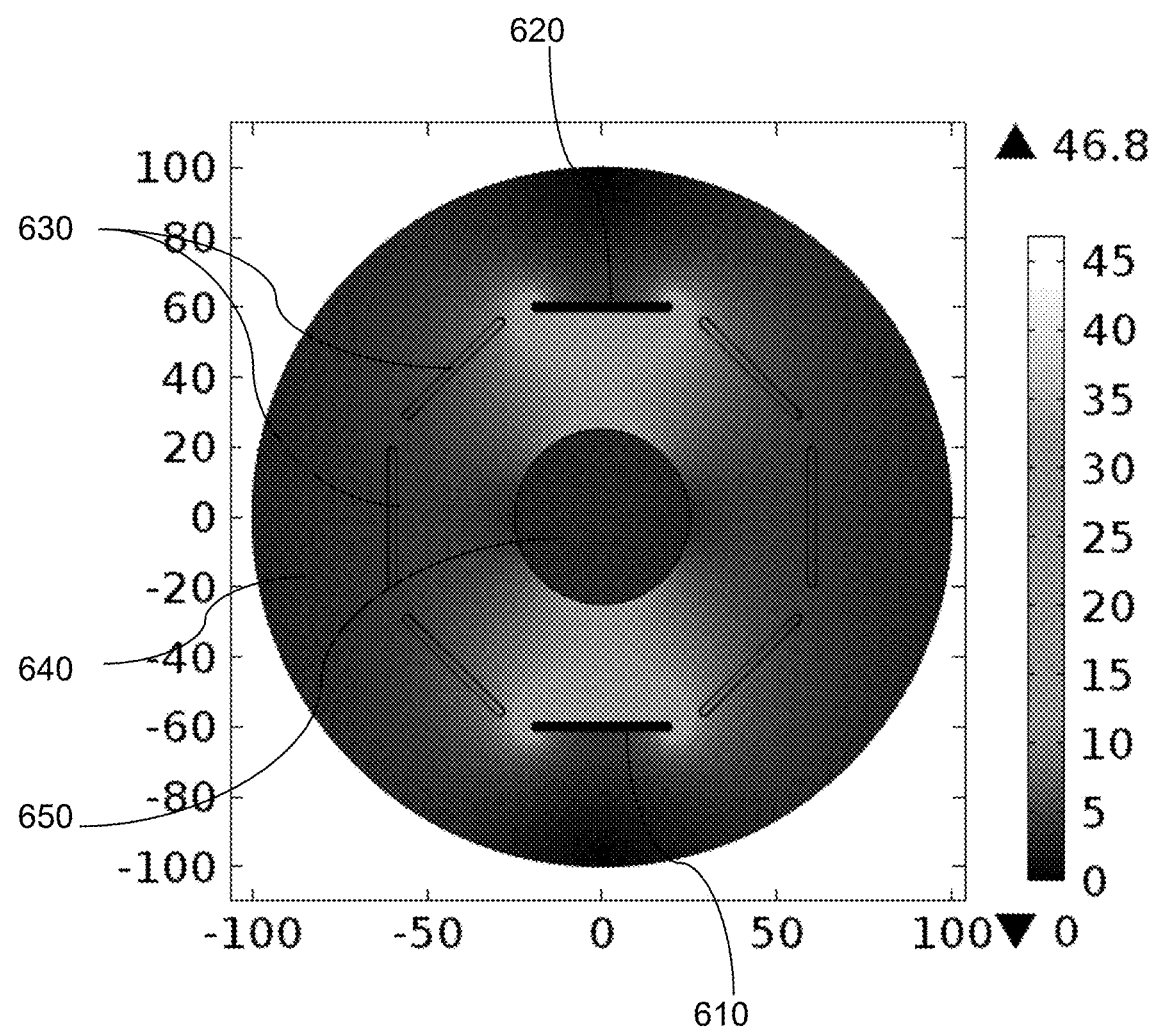
FIG. 6 is a simulated electric field within an 8 electrode ECT sensor, where air fills the void space between the electrodes and circular nylon target (center)
Figure 7:
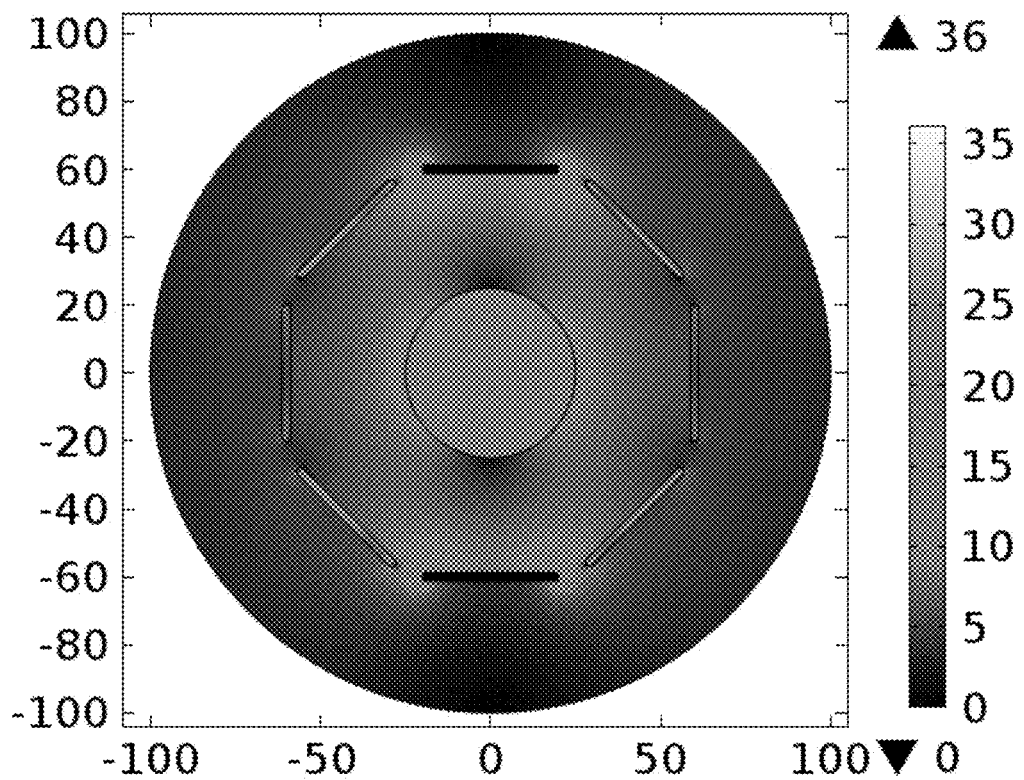
FIG. 7 shows an identical simulation to FIG. 6, where ethylene glycol fills the void space between the electrodes and target.
Figure 8:
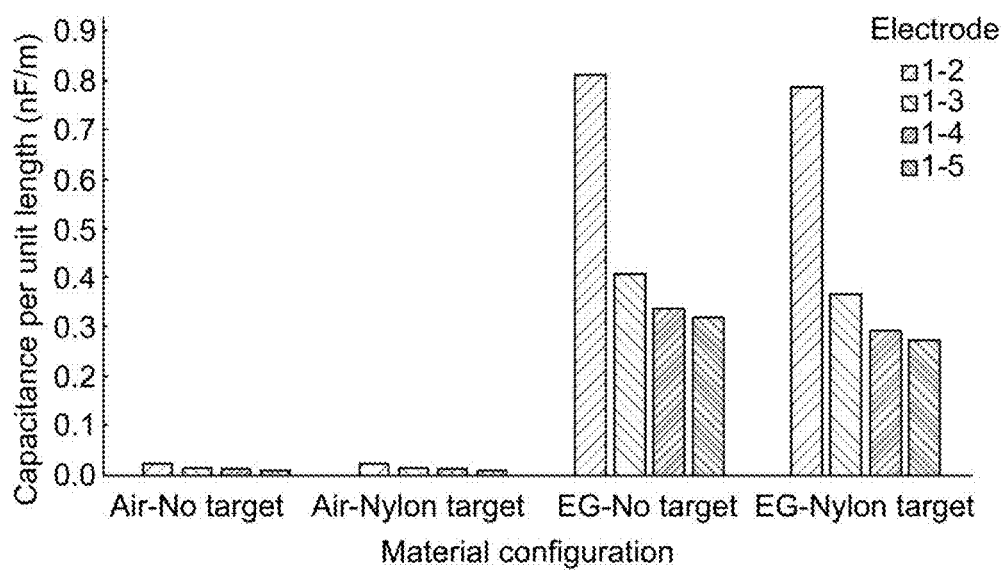
FIG. 8 plots the simulated inter-electrode capacitances as a function of fluid configuration, target presence, and electrode pairs.
Figure 9:
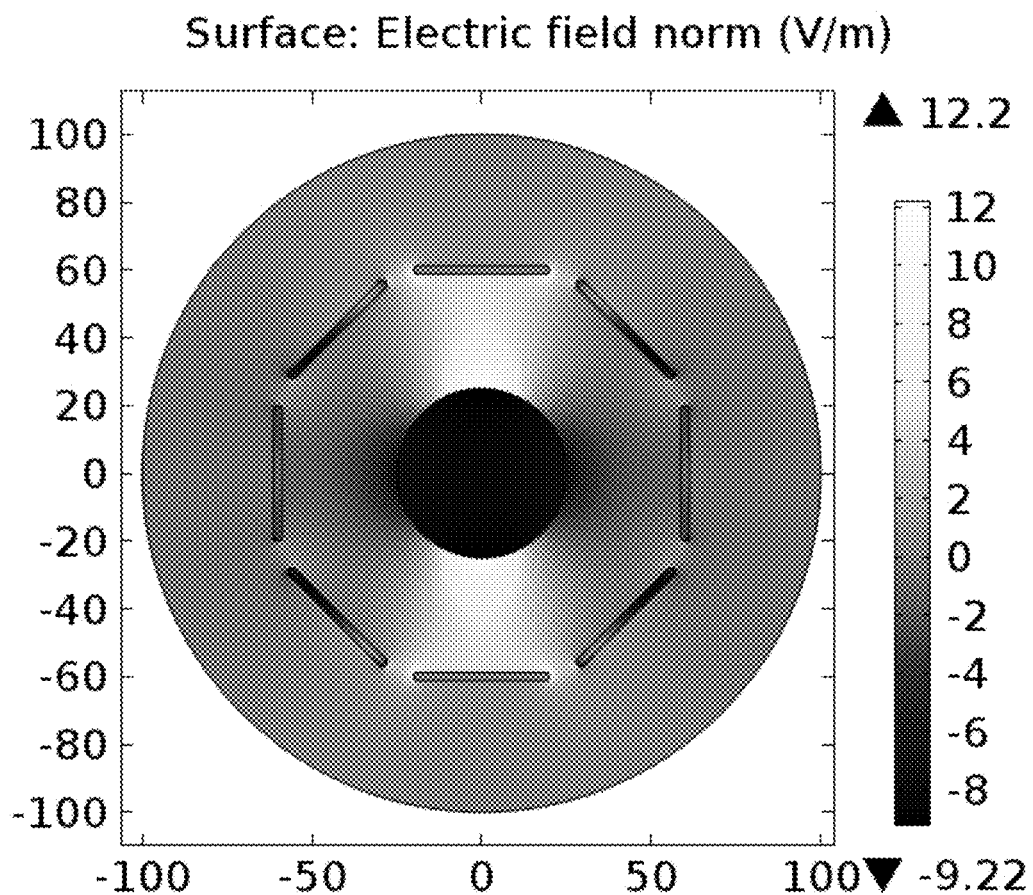
FIG. 9 plots the difference in electric field norm between the results shown in FIGS. 6 and 7, showing that the sensitivity map has changed as a function of fluid configuration.
Figure 10:
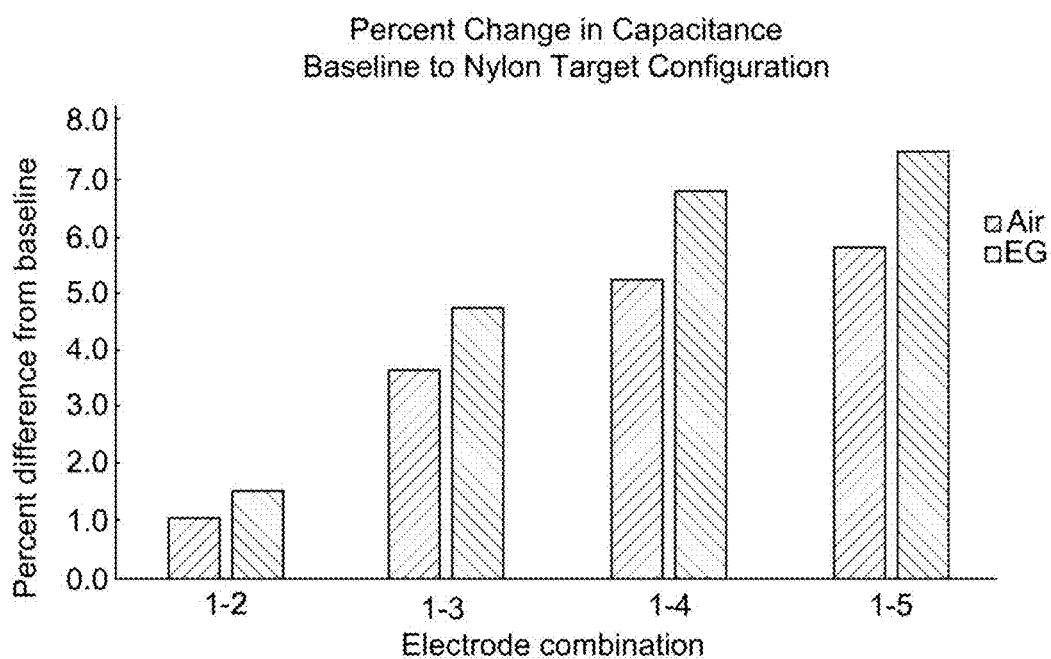
FIG. 10 presents the results of FIG. 8 as percent change in measurement as a function of target presence.

To demonstrate the effectiveness of such a fluid configuration, we have developed a 2D Finite Element Analysis (FEA) simulation of the ECT process using COMSOL (Burlington, MA). The geometry and a typical result of the simulation is shown in FIG. 6, in which a circular nylon target 650 has been placed within an 8 electrode sensor. COMSOL solves the equations developed above to calculate the capacitance between the sensing electrode 610 and excitation electrode 620, by way of the electric field norm 640. Inactive electrodes electrically float 630. The simulation was performed first using air, again shown in FIG. 6, as the void-filling fluid ($\epsilon_r=1.00$) to provide a measurement representative of conventional ECT technology. An identical simulation using an ethylene glycol fluid configuration as a ($\epsilon_r=37$) as a contrast agent is shown in FIG. 7. The calculated inter-electrode capacitances are plotted in FIG. 8 for all combinations of fluid and target presence. Clearly, using ethylene glycol as a contrast agent provides one the luxury of measuring larger capacitances, and larger changes thereof. Moreover, these data show that sensitivity is changed in two ways, the first being a direct result of the discussion in the above paragraph. More subtly, however, the contrast agent changes the electric field by concentrating it in the region directly between electrodes, even when no target is present. Graphically, this redistribution in electric field is shown in FIG. 9 by plotting the difference between FIG. 6 and FIG. 7. This second effect becomes clear in the numerical results plotted in FIG. 10; if the enhanced capacitance was simply due to the first effect, the increase in measured capacitance would increase in proportion to A, and there would be no difference in the percent change of the sensor readings. However, these data show that redistribution of the electric field provides a second mechanism by which the sensitivity map is altered.

Figure 11:
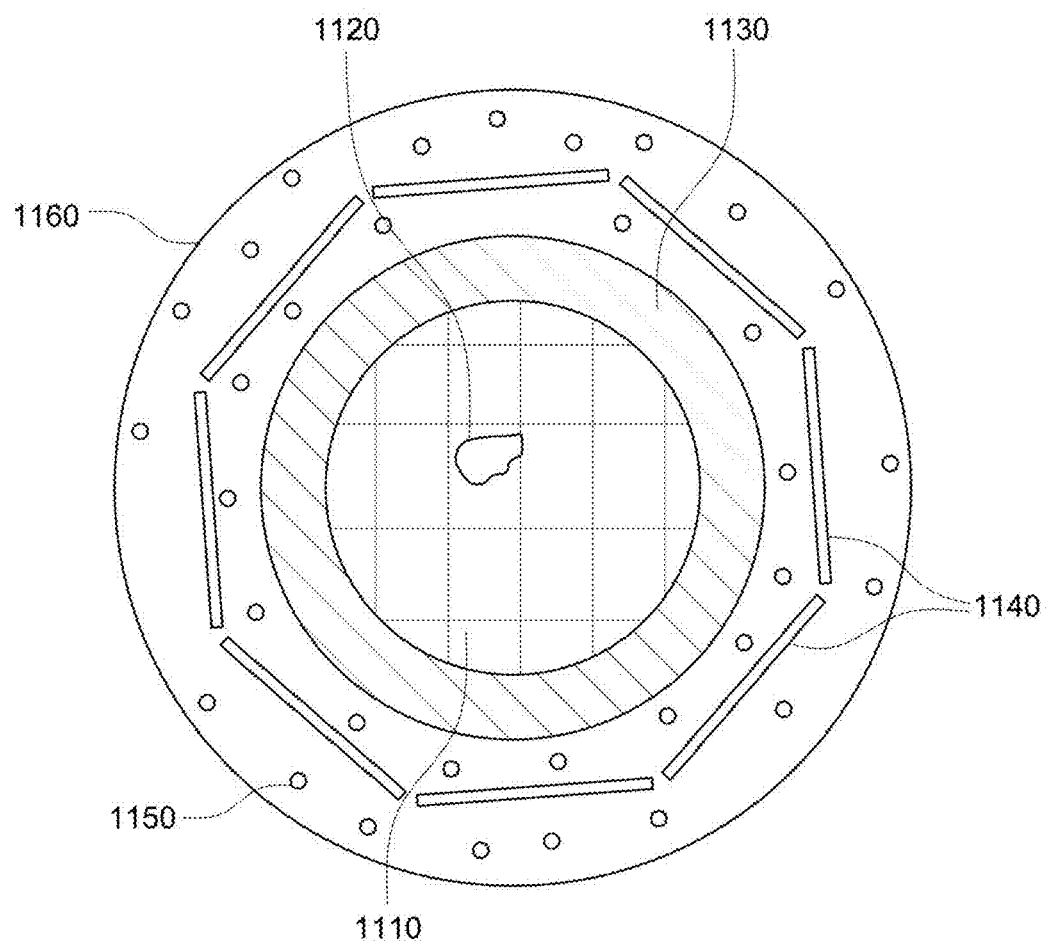
FIG. 11 shows a fluid configuration used to mask a material that otherwise clutters the target material and defect.

In other embodiments, it may be advantageous to mask the effects of certain materials within an ECT, ERT, or EIT sensor, as illustrated in FIG. 11. In this figure, we show a situation in which the geometry of the inner material 1110 is critical to component function; however, a surrounding material 1130 impedes direct measurement. By eliminating signal contributions at the sensing electrodes 1140 from the outer, non-critical material with a carefully chosen fluid configuration 1150 contained in a vessel 1160, one is able to perform clutter-rejection in hardware and improve the fidelity with which the critical sub-component is imaged. Alternatively, one could envision the need to inspect a solid polyethylene ($\epsilon_r=2.25$) component for porosity 1120 for use in a high performance or mission-critical application. If the component is placed in a conventional, air-filled sensor, the reconstruction algorithm is then challenged to separate contributions from the bulk of the component, which is not of interest, from the air-filled voids it may contain. By selecting a suitable masking agent to fill the void space, carbon tetrachloride ($\epsilon_r=2.238$) would be suitable, the reconstruction algorithm is faced with a much simpler task of finding defects in the component in a clutter-free environment.

In contrast to ECT, where an ambient fluid of low conductivity may be advantageous, ERT and EIT rely on maintaining some degree of electrical conductivity through the sensing volume. In these sensing modalities, the electrodes are often directly attached to the target. Such implementations are disadvantageous for three reasons. First, small, random errors in electrode placement manifest as large errors in reconstructions; this is an especially difficult problem when sensors are affixed to a human for medical applications. Second, the electrodes are often assumed to be placed such that they form a circular boundary, not the oblate shape of a human chest, for example. These distortions of the boundary condition results in corresponding distortions in the reconstruction. Third, the contact impedance between the sensor and subject is, in general, highly variable. This unknown interface between the electrode and the target presents a great impediment to accurate reconstruction of the electric field.

A conductive fluid permits the use of these technologies with a mechanically fixed sensor of known geometry that does not contact the subject. Filling this void space with a slightly conductive liquid, such as salt water of a controlled (and perhaps user variable) salinity, permits electrical current to flow from the electrodes, through the coupling agent, and target. In some cases, the dielectric constant and conductivity could be tuned independently, such that both the resistive and capacitive components of the impedance measurement are of the highest possible quality.

A high dynamic range electrical tomography sensor, as enabled by careful selection of a contrast, coupling, or masking agent, holds major implications for system design. Typically, ECT sensor designs contain 8 to 12 electrodes, arranged circularly about a diameter approximately half of the length of each electrode in the axial direction. Such an aspect ratio is necessary to ensure that small changes in the permittivity distribution inside the sensor are manifest as large enough changes in capacitance to be measured. This has an averaging effect, as the X-Y image that is reconstructed is actually a representation of the X-Y permittivity distribution averaged over the entire Z (axial) length of the detector. For measuring many targets, an axial resolution on the order of centimeters to tens of centimeters is inadequate to resolve features of interest. With our system, it would be possible to offset the increase in sensitivity from filling the void space with a well-chosen fluid by shortening the length of the electrodes in the axial direction. Thus, one may reduce this averaging effect by shortening the sensor electrodes, all while maintaining suitable signal size as compared to readout sensitivity.

Either as an alternative, or in addition, one can decrease the length of the electrodes in-plane, thereby increasing the number of electrodes that may be arranged around the area of interest. Even modestly increasing the number of sensing electrodes greatly increases the number of possible independent capacitance, resistance, or impedance measurements possible. These additional measurements reduce the ill-possedness of the reconstruction, enabling more accurate and higher resolution reconstructions to be generated. Decreasing the size of the electrodes to increase their number typically comes with a penalty in sensitivity, however, this penalty may be offset by use of a fluid configuration that enhances the signal from the device. This effect is especially applicable to the recent advances in 3D tomographic sensing using ECT, ERT, and EIT methods. For example, the signals generated by 3D ECT instruments may be orders of magnitude below a traditionally designed 2D system, and certain electrode combinations may have sensitivities so low that they can make no meaningful contribution to the reconstruction. Simultaneously, the ill-possedness of the reconstruction process is greatly increased in these systems by the need to reconstruct over a volume instead of an area. Again, a fluid configuration may be selected to increase signal magnitude and dynamic range would mitigate the effect of smaller sensing electrodes.

Figure 12:
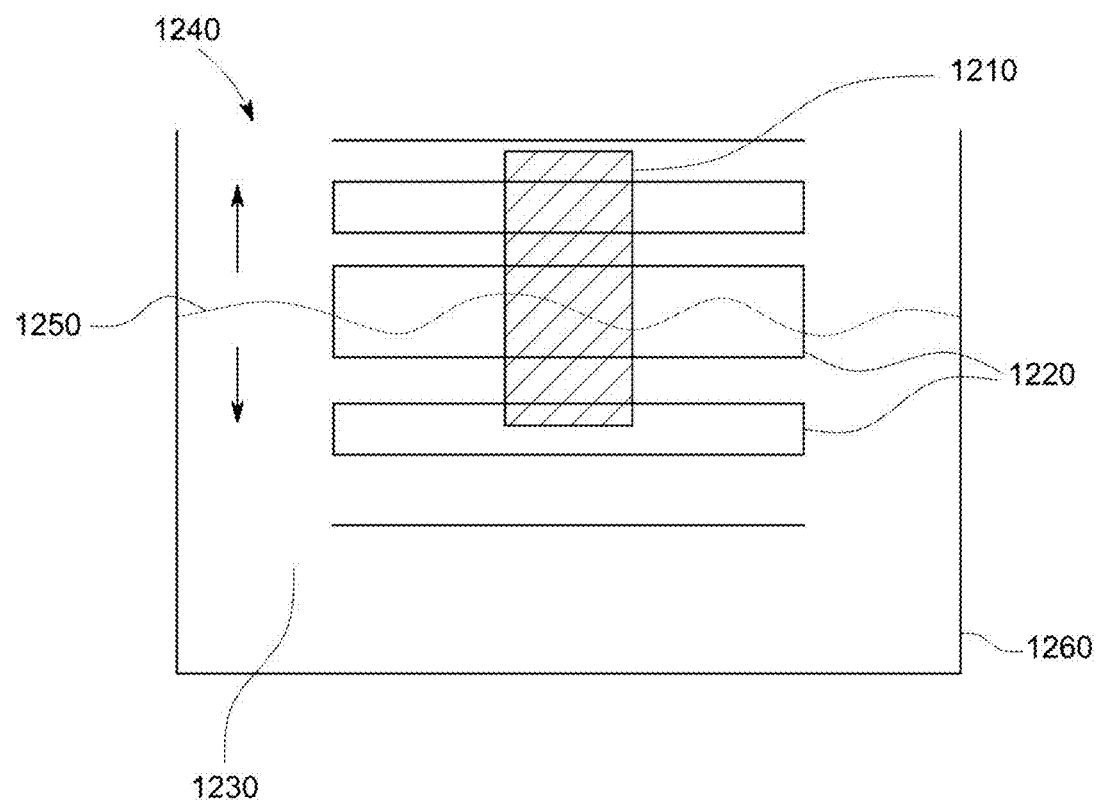
FIG. 12 shows a conventional ECT sensor oriented sideways, where a 2 part fluid configuration is used to manipulate the sensitivity maps within the sensor.

Manipulating the sensitivity of the sensor in other ways may be of benefit. Consider the system illustrated in FIG. 12. Here, the effective sensitivity maps may be altered by changing the relative levels of the fluids 1230 and 1240 within the sensor vessel 1260; optimally this boundary 1250 would be actively sensed to compensate for target displacement. Each set of measurements between sensing electrodes 1220 at a given fluid boundary height become useful for determination of the target 1210 shape.

Figure 13:
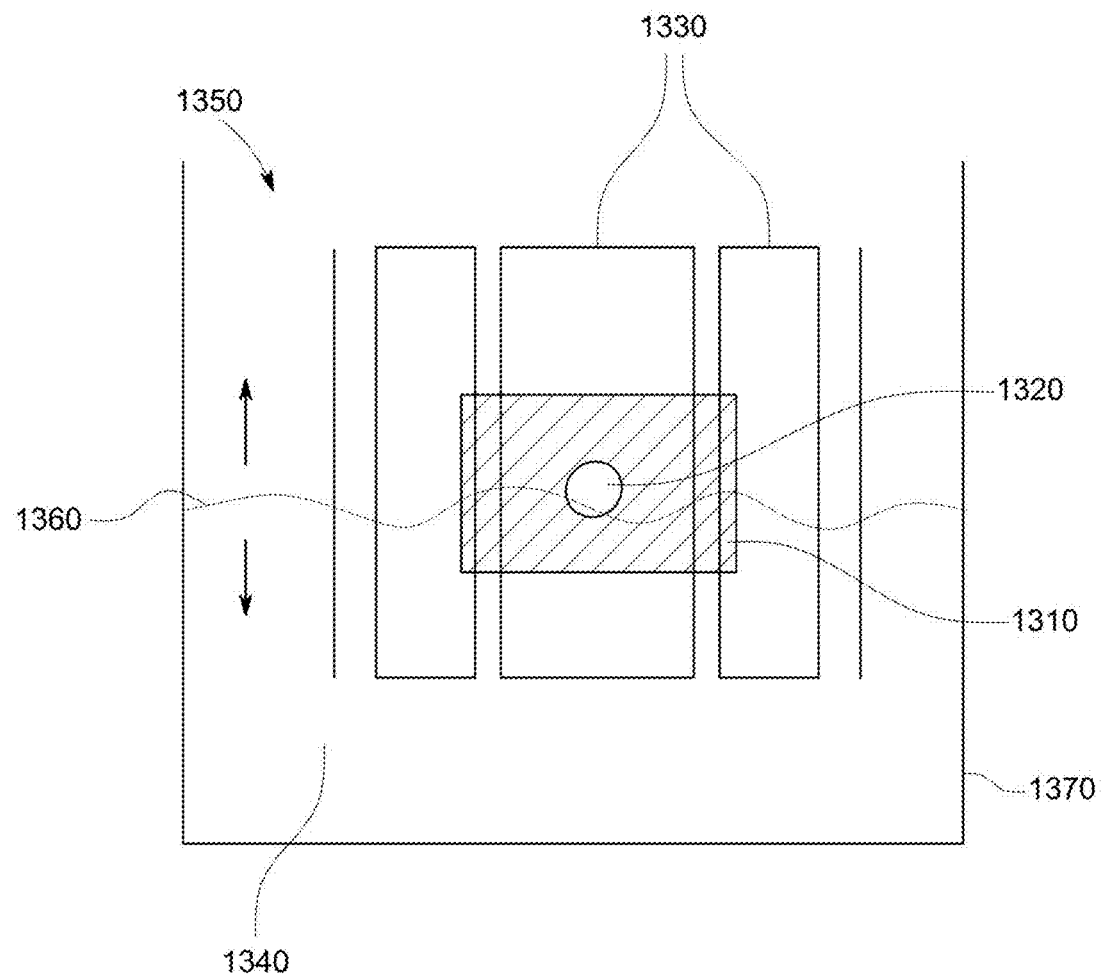
FIG. 13 shows a conventional ECT sensor oriented vertically, where a 2 part fluid configuration is used to alter 3D sensitivity maps within the sensor along the axial direction, thereby enabling 3D reconstruction.

Moreover, a configuration such as that shown in FIG. 13 may be used to extend the effective dimensionality of a sensor. Under typical operation, such a sensor effectively measures the average properties along the axial direction of the sensor. However, measurement of this two-fluid configuration enables the sensitivity mapping in the axial direction to be changed dynamically. For example, if fluid 2 1350 is of very low dielectric constant, then the signal substantially results from the combination of fluid 1 1340 and the target 1310, between the sensing electrodes 1330. Measurement at a range of interface heights 1360 between fluid 1 and fluid 2 then enables the shape of the target in the axial direction to be resolved, including the ability to axially resolve defect location 1320. Again, the fluid configuration is maintained via containment vessel 1370.

Application of a plurality of fluid configurations may improve reconstruction by providing more independent measurements of the sensed volume. As discussed above, changing the working fluid within the sensor changes the sensitivity maps between electrodes. Essentially then, one is able to increase the number of independent measurements beyond that specified in Eqn. 5 for reconstruction, in direct proportion to the number of fluids used.

Moreover, providing a plurality of surrounding fluids provides novel means for regularizing the inverse reconstruction problem, as previously introduced. The inversion process may be weighted to penalize the reconstruction based upon prior knowledge of the system, augmented here by the different fluids used. Consider the case of a complete set of intra-electrode measurements of a target, taken as small changes are made to the dielectric nature of the surrounding fluid. The algorithm may then penalize sharp changes in the shape of the target region reconstruction as a function of contrast agent dielectric constant. This method may be further augmented by conventional regularization methods, including penalization of large first or second spatial derivatives of the measured properties.

While there are an infinite number of applications of the concepts listed above, here we detail two potential applications of great potential. Specifically, we detail an outstanding need for low-cost, ruggedized medical imaging kit service remote and impoverished areas. Finally, an alternative application in an industrial setting is treated in quality and process control for a continuous polymer extrusion process.

Figure 14:
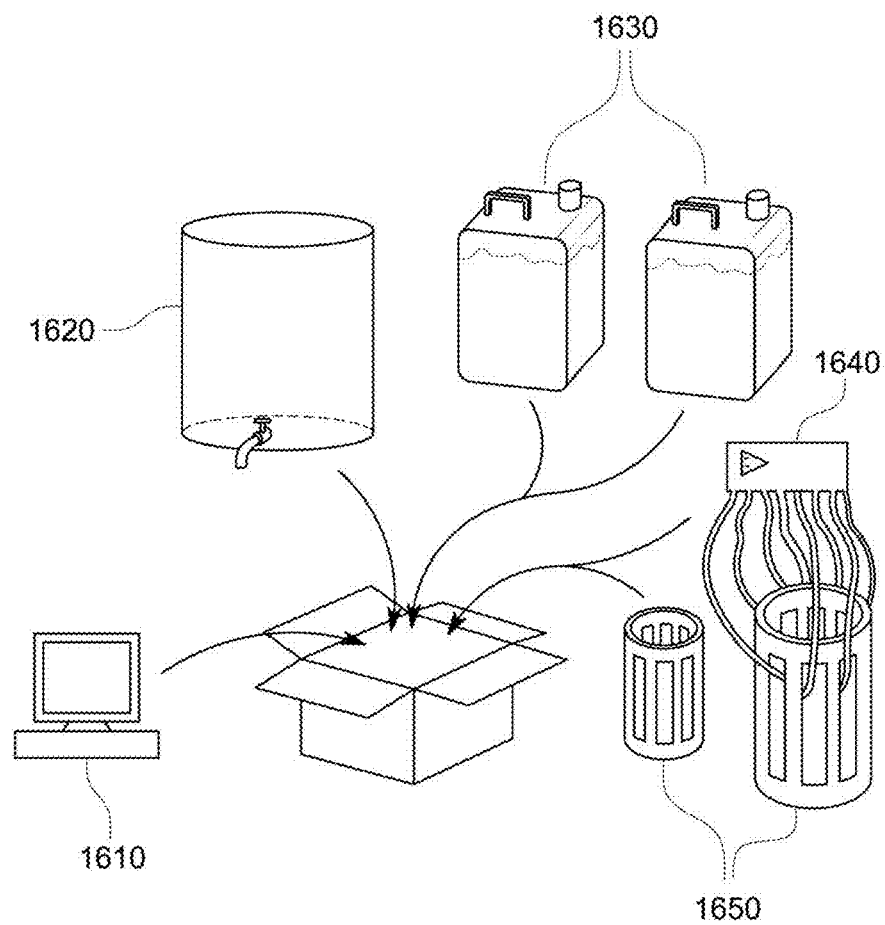
FIG. 14 shows the elements of a kit for performing tomography by electrical properties in remote locations.

Here, a novel kit intended for medical imaging in remote areas is described, comprising a ruggedized sensor and fluid configurations. Centrally, the sensor is designed with mechanically fixed electrodes disposed about a known boundary, thus the electrodes remain perfectly positioned throughout data collection. The kit includes multiple easy to use parts, as seen in FIG. 14. The kit specifically contains: sensors of different sizes with standardized electrical connectors 1650; contrast, masking, or coupling agents 1630; container(s) to hold the fluids above 1620, optimally labeled with relevant safety and electrical property information; electrical readout to measure sensor impedance 1640; and a computer with monitor to process and display images 1610.

The function of this kit is to allow rapid tests for diagnostic purposes. Individuals can choose the most appropriately sized sensor (the sensor that is smallest but still fits around the patent's area of concern). The user then fills the container with a fluid configuration and submerges the sensor with the patient's area of interest in it. In some cases, the fluid configuration may be selected to reduce the effective contact resistance between the sensing electrodes and patient, reducing measurement uncertainty induced thereby. In addition, or alternatively, the fluid configuration may be chosen to highlight tissue types of interest by employing the principles disclosed herein.

The container may also include a drain so the liquid can be quickly removed and returned to a storage or disposal container. It is important to note that allowing a fast and easy way to drain the medium can allow the physician to employ a plurality of fluid configurations, limited only by considerations of patient safety.

It is also known that salt changes the resistivity of a solution, as is central to the function of ERT and EIT sensing modalities. An alternate design of this kit includes a single contrast medium, water and a container of salt. The user can manually alter the resistivity of the contrast agent by adding salt directly to the medium. This offers the benefit of greatly reducing the size of the kit.

An alternate application lies in the fabrication of dielectric material pipelines (i.e. polyethylene pipes). These pipes have safety and quality regulations that have to be followed similarly to conventional metal pipes. These regulations are important as any leak in pipelines can cause significant safety, environmental, and economical damage. To verify pipe integrity, there are multiple Non-Destructive Evaluation (NDE, also commonly seen as Non-Destructive Testing or NDT) methods for metal pipes; however, many of them cannot be reliably applied to dielectric pipes owing to the significant difference in material properties between these two classes of materials. Electrical capacitance tomography has been proposed as an inspection technology for these pipelines as it has been used in other NDE applications. This is due to the rapid and inexpensive nature of data collection through ECT. However, the low spatial resolution is a significant hurdle to overcome in applying traditionally-implemented ECT to NDE.

This hurdle may be overcome by attaching a fluid configuration-filled sensor that pipelines pass through just after they are formed via an extrusion process. The sensor may mechanically attach to the extrusion die, such that the freshly extruded pipe is continuously inspected as it comes out of the machine (is fabricated).

Figure 15:
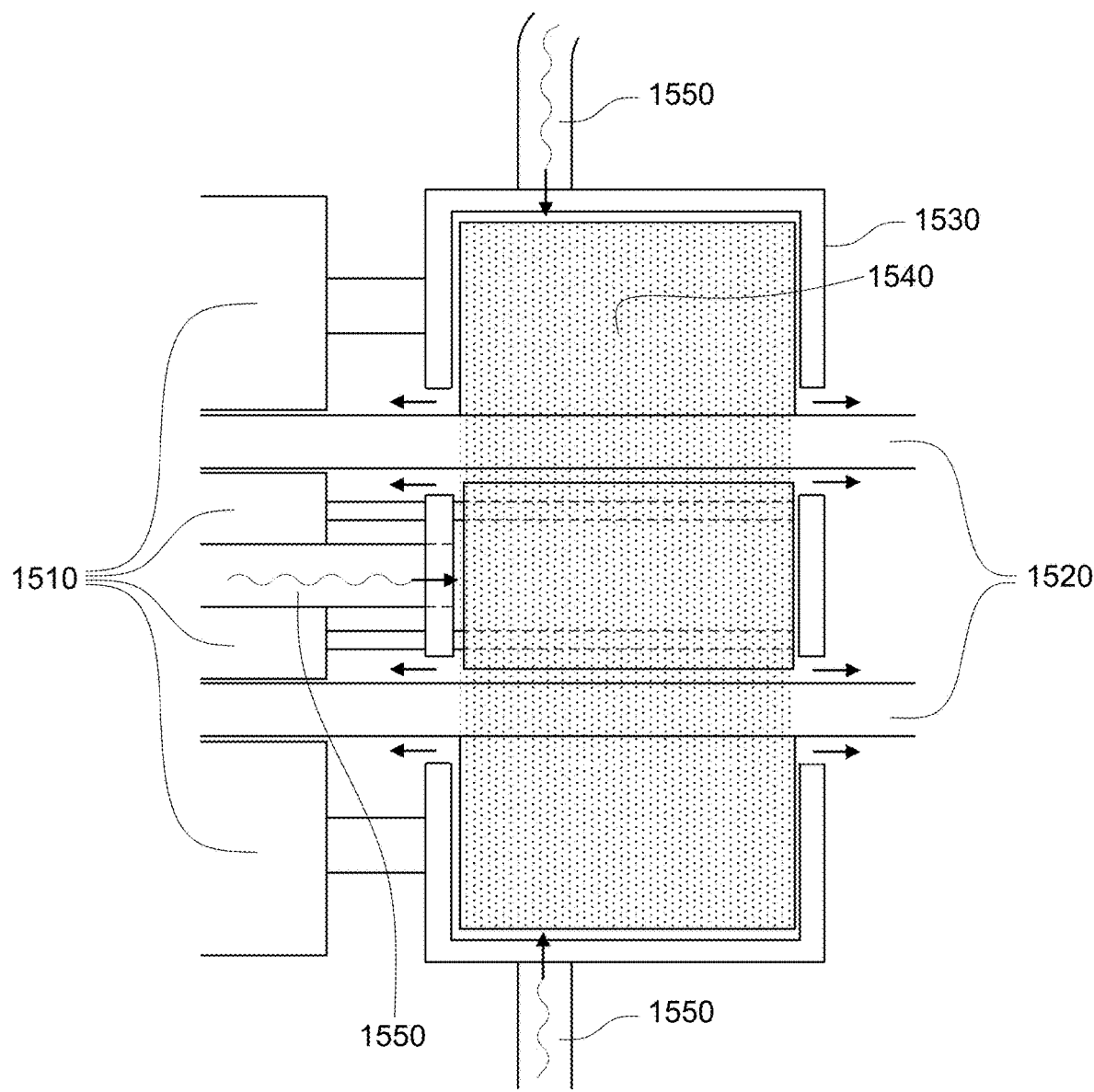
FIG. 15 shows an ECT sensor affixed to a continuous-extrusion die, fabricating a polymer tube, that enables quality control.

An example of how this may be accomplished is depicted in cross-section by FIG. 15, which includes attaching an ECT enclosure 1530 to the extrusion die 1510 exterior and mounting the ECT plates within this enclosure. Fluids 1550 can then be pumped into the enclosure both to regions exterior and interior to the finished pipe 1520. The enclosures include an opening large enough to allow the pipe to pass through it, but close enough to only allow a small amount of the contrast agent to escape. This minute amount of contrast agent escaping does not pose a problem, as it may be pumped back into the enclosure through a recirculating loop. Principle directions of fluid flow are depicted by arrows. As only the short length of tube in the sensed region 1540 is imaged at one time, axial resolution is high as compared to the length of pipe that may be produced.

Figure 16:
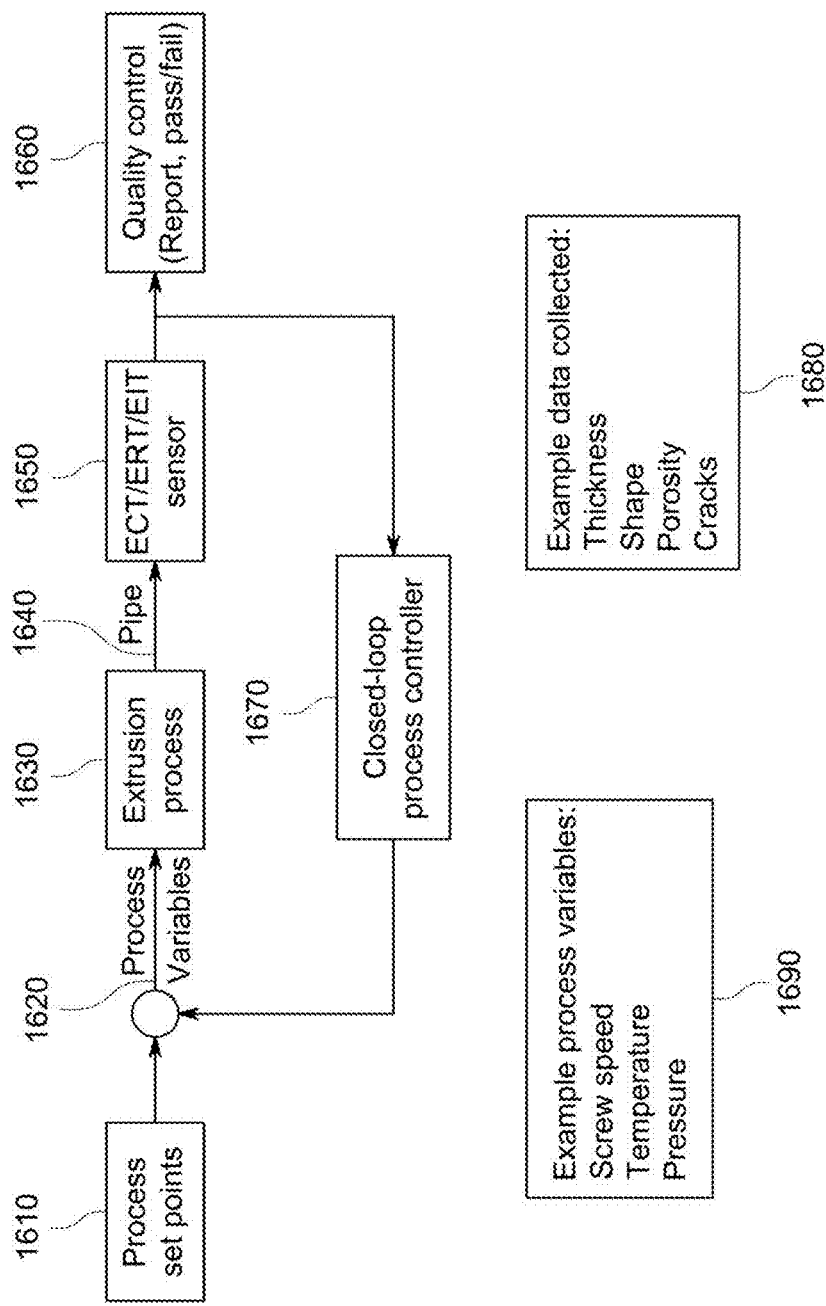
FIG. 16 shows how measurements from the system shown in FIG. 15 may be employed for process control.

This tomographic method may also provide measurement for process control, as depicted by the block diagram in FIG. 16 for an exemplary pipe extrusion process. Process parameters 1690 such as screw speed, temperature or pressure may be adjusted. During the process, the sensor 1650 (ECT, ERT, or EIT) collects data around the pipe 1640, that are subsequently used to form a cross-sectional image. From here, image processing methods may be employed to extract pipe parameters 1680 including thickness and form, and finally note any crack developments or porosity for quality control 1660. Thickness and form data are then used to inform adjustments to the process variables by a controller 1670 to achieve process setpoints 1610. Electrical tomography is an ideal imaging technique for use in closed loop feedback control, as its high sample rate (hundreds of Hertz) enable the controller to change the set points in a timely fashion.

We claim:

1. A method for performing tomography via recovery of a distribution of an electrical property comprising the steps of:
   providing a target object or portion thereof to be imaged;
   providing a plurality of sensing electrodes with a known geometric configuration;
   geometrically configuring the target object and the electrodes to place the target object within a region effectively sensed by the electrodes;
   filling the void space between the target object and the plurality of electrodes with a fluid configuration comprising at least two immiscible fluids with known boundary heights by changing the relative levels of the immiscible fluids;
   making electrical measurements between the electrodes;
   computing sensor sensitivity maps using the known electrical properties of the fluid configuration, the known boundary heights of the fluid configuration, and the known geometry of the electrodes; and
   mathematically inverting the electrical measurements to recover a reconstruction of the electrical property within a volume using a computational device configured to receive the measurements using the sensor sensitivity maps.

2. The method of claim 1, further comprising the step of adapting at least one fluid of the fluid configuration to contrast the electrical properties of a material known or suspected to at least in part comprise the target object.

3. The method of claim 1, further comprising the step of adapting at least one fluid of the fluid configuration to mask the signal contribution of a material known or suspected to at least in part comprise the target object.

4. The method of claim 1, further comprising the step of adapting at least one fluid of the fluid configuration to improve coupling of an electrical property between the electrodes, the target object, or a constituent fluid within the fluid configuration.

5. The method of claim 1, further comprising mathematically encoding known electrical properties of the fluid configuration into a prior and applying the encoded prior to regularize the inversion process.

6. A method for performing tomography via recovery of a distribution of an electrical property comprising the steps of:
   providing a target object or portion thereof to be imaged;
   providing a plurality of sensing electrodes with a known geometric configuration;
   geometrically configuring the target object and the electrodes to place the target within a region effectively sensed by the electrodes;
   for each of a plurality of distinct fluid configurations comprising at least two immiscible fluids wherein each of the fluid configurations has known boundary heights, (i) filling a void space between the target and the plurality of electrodes with the fluid configuration; (ii) making electrical measurements between pairs of the electrodes;
   computing sensor sensitivity maps using the known electrical properties of the fluid configurations, the known boundary heights of the fluid configurations, and the known geometry of the electrodes; and
   and mathematically inverting the electrical measurements to recover a reconstruction of the electrical property within a volume using a computational device configured to receive the measurements using the sensor sensitivity maps.

7. The method of claim 6, wherein the sensing electrodes are arranged in a known two dimensional geometric configuration, and further comprising adapting the boundary heights of the fluid configurations to provide spatial resolution of the reconstruction along a third geometric axis.

8. The method of claim 6, further comprising mathematically encoding known electrical properties of each distinct fluid configuration into a prior and applying the encoded prior to regularize the inversion process.

9. A system for performing tomography via recovery of a distribution of an electrical property comprising:
   a plurality of sensing electrodes with a known geometric configuration;
   a measuring circuit for making electrical measurements between the electrodes;
   a fluid configuration comprising at least two immiscible fluids with known boundary heights; and
   a computational system configured to receive the electrical measurements, known electrical properties of the fluids, and the known boundary height of the fluid configuration, compute sensor sensitivity maps corresponding to the fluid configuration, and invert the measurements to recover the distribution of the electrical property within a volume using the sensor sensitivity maps.

10. The system of claim 9, wherein at least one fluid of the fluid configuration contrasts the electrical properties of the nominal target material.

11. The system of claim 9, wherein at least one fluid of the fluid configuration masks signal contributions from the electrical properties of the nominal target material.

12. The system of claim 9, wherein at least one fluid of the fluid configuration is to improve coupling of an electrical property between the electrodes, the nominal target material, or constituent fluid within the fluid configuration.

13. The system of claim 9, further comprising a plurality of fluid configurations.

14. The system of claim 9, further comprising a plurality of fluids or fluid components for altering the fluid configuration.

15. The system of claim 14, further comprising a pump to achieve a specified fluid configuration, by introducing or removing fluid or component of a fluid into the fluid configuration.

16. The system of claim 9, further comprising a containment vessel to substantially contain the fluid configuration.

* * * * *